United States Patent [19]
Estrin

[11] Patent Number: 6,139,829
[45] Date of Patent: Oct. 31, 2000

[54] SKIN WRINKLE TREATMENT WITH IONIC POLYMERS

[76] Inventor: Norman Estrin, 9109 Copenhaver Dr., Potomac, Md. 20854

[21] Appl. No.: 09/167,003

[22] Filed: Sep. 25, 1998

[51] Int. Cl.⁷ .............................. A61K 9/10; A61K 7/48; A61K 7/04
[52] U.S. Cl. ..................................... 424/78.08; 424/78.03
[58] Field of Search ............................... 424/78.08, 78.03

[56] References Cited

U.S. PATENT DOCUMENTS

| | | | |
|---|---|---|---|
| 4,665,107 | 5/1987 | Micale | 523/105 |
| 5,885,564 | 3/1999 | Zastrow et al. | 424/74 |

FOREIGN PATENT DOCUMENTS

0514760A1  11/1992  European Pat. Off. .

OTHER PUBLICATIONS

"Parfums, Cosmetiques, Aromes" 72, Dec. 1986 pp. 61–64.

*Primary Examiner*—Peter F. Kulkosky

[57] ABSTRACT

This invention designs cosmetic compositions for improving the appearance of skin and nails. The invention provides a cosmetically acceptable composition for removing the appearance of wrinkles and for hardening nails. A method for reducing the appearance of wrinkles according to the invention comprises applying to the skin a cosmetic composition comprising an effective amount of a superabsorbent ionic: polymer or copolymer comprising acrylate and/or acrylamide monomers or other suitable highly hydrophilic polymer in a topically acceptable vehicle, and allowing the vehicle to dry, so as to immediately and temporarily reduce all appearance of wrinkles without forming a visible film. The invention also encompasses a method for hardening nails, comprising repeatedly applying to the nails a cosmetic composition comprising an effective amount of a polymer of an acrylamide and/or acrylate monomer in an acceptable vehicle, so as to cause a desirable hardening of the nails after repeated use.

13 Claims, No Drawings

SKIN WRINKLE TREATMENT WITH IONIC POLYMERS

BACKGROUND—FIELD OF INVENTION

This invention relates to cosmetic compositions for improving the appearance of skin and nails. Specifically, the invention relates to compositions comprising superabsorbant ionic polymers such as polymers and copolymers of acrylate salt polymers in compatible vehicles, and methods of application and preparation.

Wrinkled skin presents a perceived problem for many people who wish to improve their appearance immediately. There is an enormous demand for cosmetic formulations that reduce wrinkles or the appearance of wrinkles. Few products claim to do this immediately. Serum albumin has been used to reduce the appearance of wrinkles in a commercial product called Sudden Change, distributed by CCS Industries, East Rutherford, N.J. 07073. This product tightens skin immediately but is uncomfortable to use and leaves an unsightly white film. U.S. Pat. No. 4,777,041 describes a wrinkle treatment formulation comprising a gelable hydrophylic polyutherane and a precipitated silica thickener gelling agent which fills wrinkles when dried. The polyutherane and silica components have various undesirable properties that make such a composition unsuitable for widespread use.

Other anti-wrinkle formulations have been sold but these do not act immediately. In general, existing anti-wrinkle products may take months to show an effect. Still, other products affect the structure and function of the body and would be considered to be drugs by the Food and Drugs Administration, and subject to extensive regulation. One such product manufactured by Johnson & Johnson, is Renova. This product is considered to be a prescription drug by the FDA. In addition, many products on the market make claims that are unsubstantiated and subject to regulatory action by the FDA or by the Federal Trade Commission.

OBJECTS AND ADVANTAGES

This invention satisfies a long felt need for a cosmetically acceptable composition and methods for reducing the appearance of wrinkles. The invention succeeds where previous efforts at providing a cosmetically acceptable composition for removing the appearance of wrinkles have failed, and solves other problems previously addressed by existing products in an unsatisfactory manner. The invention is in the crowded and and mature art of cosmetic formulations, including wrinkle treatment formulations. Even in this crowded market, few products can claim and substantiate instant anti-wrinkle effects.

The differences between the invention and the prior art are modifications that were not previously known or suggested, including die particular polymer components employed and the methods of their use. One of the preferred polymers, polyacrylamide/polyacrylate copolymer, is an agricultural ingredient never before used in cosmetic products. Another, crosslinked sodium polyacrylate, have never been marketed to the cosmetic industry for this purpose. The compositions and methods of the invention provide advantages that were not previously appreciated for the individual components of the composition.

A method for reducing the appearance of wrinkles according to the invention comprises applying to the skin a cosmetic composition comprising an effective amount of a superabsorbent ionic: polymer or copolymer comprising acrylate and/or acrylamide monomers or other suitable highly hydrophilic polymer in a topically acceptable vehicle, and allowing the vehicle to dry, so as to immediately and temporarily reduce the appearance of wrinkles without forming a visible film. The method provides the sensation of cooling of the skin. The method may further comprise applying a hydrating lotion to the skin after the cosmetic composition has dried.

A cosmetic composition according to the invention comprises an effective per dose amount of a superabsorbent ionic polymer selected from the group consisting of a polymer of an acrylate salt, an ionic copolymer of acrylate and acrylamide, and a combination, in a topically acceptable vehicle, the composition being, non-irritating when applied to the skin. The polymer preferably comprises a copolymer of acrylamide and sodium acrylate and, in addition, crosslinked sodium polyacrylate, preferably in a ratio of about 10: I or less. The composition preferably includes a preservative. The composition is effective to immediately and temporarily reduce the appearance of wrinkles when applied to the skin.

The composition is preferably free of oily components, and the polymer is in the form of a homogeneous distribution of fine particles.

In another embodiment of the invention, inventive compositions harden nails desirably and lastingly when applied repeatedly over an extended period. These compositions also soften cuticles. There are several cosmetic products on the market or in the patent literature for improving the appearance and durability of nails. Existing nail hardening products have various disadvantages including the use of toxic or unpleasant vehicles, and lack the ability to provide harder nails over an extended period. There are relatively few effective products and these involve the use of potentially allergenic/irritating chemicals.

The invention also encompasses a method for hardening nails, comprising repeatedly applying to the nails a cosmetic composition comprising an effective amount of a polymer of an acrylamide and/or acrylate monomer in an acceptable vehicle, so as to cause a desirable hardening of the nails after repeated use. The method softens cuticles. The composition is applied to the nails one to three times daily over an extended period, such as three days to three weeks. After that period, the inventive compositions and method produces measurable improvements in uniformity of color, polished appearance, strength and hardness, decreased splitting, peeling, and breakage, and condition of cuticles. Users view such a composition as something they would purchase, so that it is a commercially viable composition.

Further objectives and advantages will become apparent from a consideration of the description, and examples.

SUMMARY

In summary the present invention relates to a composition comprising a superabosorbant hydrophylic component, other optional beneficial ingredients and a cosmetically acceptable vehicle. The polymer component preferable is a combination of a cross linked sodium polyacrylate and a copolymer of sodium acrylate and acrylamide. The composition removes the appearance of wrinkles almost immediately upon application, leaving no unsightly film. These products are free from irritating components and will likely have the advantage of avoiding regulation as drugs because of their temporary effects.

PREFERRED EMBODIMENT—DESCRIPTION

In describing preferred embodiment, of the present invention illustrated, specific examples are employed for the sake of clarity. However, the invention is not intended to be limited to the specific examples so selected, and it is to be understood that each specific element includes all technical equivalents which operate in a similar manner to accomplish a similar purpose.

The compositions of the invention comprise suitable superabsorbent polymers, distributed homogeneously in an aqueous vehicle, and preferably comprise a preservative. A method of the invention comprises applying the composition to achieve a cosmetically desirable result, selected from applying to the skin so as to immediately and temporarily reduce the appearance of wrinkles without forming a visible film.

Preferred polymers according to the invention are copolymers containing acrylamide and acrylic acid salt monomers. Tile copolymers may be alternating copolymers, random copolymers, block copolymers, or graft copolymers. They may be linear or branched, and are optionally cross-linked. Particularly preferred polymers are: a copolymer of acrylamide and sodium acrylate sold by Allied Colloids, Inc. under the trade name ALCOSORB AB3C; a copolymer of acrylamide and sodium acrylate sold by Grain Processing Corporation under the trade name Water Lock A-400 Series; a copolymer of starch, with grafted side chains of copolymers of acrylamide and sodium acrylate, sold by Grain Processing Corporation, under the trade name Water Lock, A-100 Series. Other suitable polymers include a cross-linked sodium polyacrylate sold under the brand name SALSORB CL 15 (Allied Colloids Inc.).

Further cosmetically acceptable polymers of the type suitable for use in the compositions and methods of the invention include: acrylamide/ammonium acrylate copolymer,acrylamides/acrylates/DMAPA/methoxy PEG methacrylate copolymer, acrylamide\sodium acrylate copolymer, acrylamidopropyltrimonium chloride/ acrylamide copolymer, acrylamidopropyltrimonium chloride/acrylates copolymer, acrylates/ acetoacetoxyethylmethacrylate copolymer, acrylates/ acrylamide copolymer, acrylates/ammonium methacrylate copolymer, acrylates/CIO-30 alkyl acrylate crosspolymer, acrylates copolymer, acrylates/diacetoneacrylamide copolymer, acrylates/hydroxyesters acrylates copolymer, acrylates/octylacrylamide copolymer, acrylates/PVP copolymer, acrylates/steareth-20 methacrylate copolymer, acrylates/VA copolymer acrylates/VA crosspolymer, acrylates/vinyl isodecanoate crosspolymer, and acrylic acid/ acrylonitrogens copolymer. These polymers arc not known for the purposes described in this patent application. They are described further in the *International Cosmetic Ingredient Handbook*, 3rd edition, CTFA, Washington, D.C., 1995, pp. 19–21, incorporated herein by reference.

As used here, polyacrylamide is the polymer of acrylamide monomers that coxiform generally to the formula: [—CH2 CH(CONH2)-],. Polyacrylic acid is the polymer of acrylic acid that conforms to the formula: [—CH2CH (COOH)-x. Sodium polyacrylate, is the sodium salt of polyacrylic acid. A polyacrylamide/polyacrylate salt copolymer results when acrylamide and sodium acrylate are copolymerized to produce a highly cross-linked polymer.

Copolymers of acrylamide with comonomers such as acrylic and methacrylic acids are identified in Kroschwitz, ed., *Concise Encyclopedia of Polymer Science and Engineering* (Wiley 1990), pp. 13, 15. They are referred to there as polyelectrolytes or ionomers, examples of hydrogel forming polymers, p. 459. Acrylic acid and methacrylic acid and acrylate/methacrylate derivatives are discussed in Kirk-Othmer, *Concise Encyclopedia of Chemical Technology* (Wiley 1985), pp. 24–26, incorporated herein by reference.

The superabsorbent polymers according to the invention may be referred to as ionic polymers, otherwise known as ionomers, defined as polymers with inorganic salt groups attached to the polymer chain. Kroschwitz, ed., *Concise Encyclopedia of Polymer Science and Engineering* (Wiley 1990), pp. 495–97, incorporated herein by reference. Ionomers typically have about 1–10% ionic content, although other ratios are possible. They can be made by neutralizing a free acid polymer with a metal or ammonium hydroxide. The polymers of the invention may also be referred to as ionic polyelectrolytes, as in Kroschwitz pp. 789–93 and 1304–1305, and Kirk-Othmer, *Concise Encyclopedia of Chemical Technology*, (Wiley 1985), pp 923–924, incorporated herein by reference. The polymers are preferably anionic and may encompass acetate, sulfate, or phosphate functional groups such as for example polymers or copolymers of acrylic acid, methacrylic acid, vinylsulfonic acid, styrenesulfonic arid, or maleic acid. The characteristics of these compounds are strongly dependent on the ionic strength of their solution, so that salts and other electrolytes may alter the desirable characteristics of the inventive composition. The salt component of the polymers according to the invention may include, for example, sodium, potassium, lithium, and ammonium salts.

Other superabsorbent polymers such as described above, other salts, such as potassium and ammonium, and other proportions of the polymers can also be used, so long as they impart the desired effect of wrinkle-reduction or nail-hardening.

The superabsorbent polymer rapidly absorbs water and swells and has a capacity of preferably at least about 30 times its weight in water, preferably about 60 to about 100 times its weight, and feels dry when saturated to capacity. The preferred cross-linked sodium polyacrylate SALSORB CL 15 has a water capacity of about 60:1 The preferred acrylamide/sodium acrylate copolymer ALCOSORB AB3C which has a water capacity of about 100:1 (8 gallons to one lb.). The absorbency of the polymers of the invention is highest with distilled water and lower with salt solutions. For example, with WATER LOCK A-100 starch/acrylamide/ sodium acrylate polymers, the absorbency is over 160:1 for water, but only 50:1 to 60:1 for 1% NaCl.

It is surprising that these polymer compositions and combinations have the characteristics of reducing skin wrinkles, softening cuticles, hardening nails, smoothing skin and cooling skin. The *International Cosmetic Ingredient Handbook* (ICIH) is the most comprehensive list available of cosmetic ingredients as they relate to chemical class, function and product category. It was developed from dam provided to the Food and Drug Administration under Part 720 of 21 Code of Federal Regulations. According to the ICIH, polyacrylates have been reported as used in cosmetics as thickeners binders, emulsion stabilizers, film formers, and solubilizers but their effects on skin and nails have not been previously reported or recognized. Polyacrylamides are reported as used in cosmetics as binders, film formers and hair fixatives, not for the uses claimed in this patent application. (See *International Cosmetic Ingredient Handbook*, .3rd edition. CTFA, Washington. D.C., 1995).

Neither of the preferred polymers SALSORB CL-15 or ALCOSORB AB3C or any other SALSORB or ALCOSORB products are listed in the ICIH or *International Cosmetic Ingredient Dictionary*, which suggests that these ingredients are not known for cosmetic uses. SALSORB CL-15 is sold for use in adult incontinence products and ALCOSORB AB3C is marketed as a water retention aid for soil and growing media. The Water Lock, polymers are listed in the *International Cosmetic Ingredient Dictionary* and in the ICIH, but just as a "Binder; Film Former: Viscosity Increasing Agent-Aqueous."

The discovery that these products have the desired properties according to the invention is surprising and contrary to the prior art. The present invention involves radically new cosmetic uses for superabsorbent polymers such as acrylamide/sodium acrylate/copolymer, starch with grafted acrylamide/sodium acrylate copolymer, and cross-linked sodium polyacrylate, which have not been used previously for any such uses. Thus, a cosmetic composition comprising such polymers, in a suitable homogeneous preparation, packaged for use as a cosmetic to reduce the appearance of wrinkles or to harden nails, is a surprising deviation from the prior art.

The superabsorbent polymer component of the invention, and the cosmetic composition as a whole, must be non-irritating. This means that the components must not cause unacceptable irritation when the cosmetic is used as directed. The inventive compositions are free from components that would be irritating such as monomers.

The cosmetic compositions are also free from components that would interfere with the efficacy of the polymer component. The Composition is highly sensitive to addition of other ingredients and the order of addition. This is because of the electrochemical properties of the polymer. If the composition becomes "watery" after addition of an ingredient., it is likely that the product's efficacy has been impaired. Moisturizers reduce the effectiveness of the composition as a wrinkle reducer when combined with the composition or applied before the composition. Glycerin can serve as an anti-irritant component, and may be added preferably in an amount up to about 10% of the polymer component, but it decreases wrinkle-hiding effectiveness. Aloe vera gel, mineral oil, and other components interfere with the effectiveness of the composition. A dye or other colorant may be added to impart a desirable color or hue effect to the compositions.

It is highly desirable for a cosmetic composition to include a preservative. A compatible preservative is GERMABEN 11 (Sutton Laboratories), which is comprised of Diazolidinyl Urea (30%), Methylparaben (11%), Propylparaben (3%) and Propylene Glycol (56%). Other preservatives may be used so long as they do not have an ionic characteristic that would interfere with the wrinkle-hiding or nail-hardening effects of the composition. The preservatives are used in conventional amounts.

The compositions can be incorporated into a dispenser for application to the skin or nails, The dispenser is preferably labeled with an indicated method of use, as described herein.

An aspect of the invention consists of use of mixtures of superabsorbent polymers, such as those composed of polyacrylamide/polyacrylate and/or polyacrylates in various proportions, depending on the effect desired. One such composition consists of a mixture of about one part cross-linked sodium polyacrylate polymer to about nine parts copolymer of acrylate and sodium acrylate. The preferred ratio of polyacrylate/polyacrylates copolymer and polyacrylate in wrinkle removing formulations is between about 10:1 and about 1:1, preferably closer to the higher ratio, such as about 4:1 or higher. Thus, a preferred composition comprises a polymer component comprising by weight from about 33% to about 100% poly(acrylamide-sodium acrylate) copolymer and about 0% to about 67% poly-sodium acrylate. The nail composition preferably, comprises a somewhat lower ratio of poly(acrylamide-sodium acrylate) copolymer to polyacrylate but a similar range of combinations is effective for the anti-wrinkle composition. When the polyacrylamide/polyacrylate copolymer component is used independently, some irritation may result. When the polyacrylate component is used independently, the degree of wrinkle removing may be reduced. However, cosmetic compositions comprising only one or the other of the polymers may be suitable under certain circumstances.

The polymer component is preferably combined with water in a concentration by weight preferably between about 0.1% and about 10%. More preferably, the concentration is between about 0.5% and about 2%, most preferably between about 0.7% and about 1%.

Preferably the polymer is finely distributed throughout the composition so as to have a suitable consistency, homogeneity, and uniformity. This may be accomplished by.-pulverizing the polymer and thorough mixing, blending, sonication, or other techniques known in the art, to make a cosmetically appealing product.

Other proportions of the two claimed ingredients and other processing techniques can give effective compositions although not necessarily as cosmetically acceptable as the preferred compositions.

For the wrinkle remover, a single application remains in effect for an extended temporary period, generally several hours. The effect is enhanced and lengthened through use of a moisturizer several minutes after application of the composition.

PREFERRED EMBODIMENT—OPERATION

EXAMPLE 1

A formulation was prepared by the following steps:
1. Mix 0,1% Germaben II preservative system in 1500 ml water. Add any other water soluble ingredients at this time. This could include, for example, a color additive.
2. Wash sodium polyacrylate copolymer granules with alcohol or acetone, if necessary, and dry thoroughly.
3. Mix polyacrylamide/polyacrylate copolymer granules with sodium polyacrylate granules in a 9:1 ratio. Grind polymer to a fine powder.
4. Pour polymer powder into aqueous solution prepared in step 1.
5. Blend vigorously, using a sonicator.

EXAMPLE 2

The anti-wrinkle composition according to Example I is a clear gel. The finished product is odorless and colorless in the example described. It was applied to wrinkled skin in accordance with the following directions for use.

For best results, apply to clean, towel dried skin as needed to remove or soften the appearance of wrinkles. Apply several drops of gel to remove temporarily or soften the appearance of aging. Use around the eyes, on your face and on hands. Gently smooth over wrinkles and fine lines, and allow to dry. Expect to feel a cooling, pleasant tightening sensation as the composition starts to work. The product dries in about two minutes and the skin appears healthy and skin, with no sticky, greasy or unsightly flaky residue. After the gel has dried, a skin care lotion may be applied directly over treated skin. Liquid foundation and make-up may be applied as usual thereafter. The product is easily removed by washing with soap and water.

EXAMPLE 3

Test Methodology—Reducing Appearance of Wrinkles

Eight people participated as subjects in a test of the gel. Each subject was told it was to be used on the wrinkles around his/her eyes and that the protocol was to be a two-part application. One assistant was assigned the task of measuring the wrinkles on the faces of the subjects before and after application of the test material and the moisturizer. This assistant was not allowed to witness application of the test material. She drew three ovals on a piece of paper. A quick representative drawing was made of the subject's wrinkles and fine lines. A second assistant developed a numbered list of participants and arbitrarily assigned "left" or "right" to each number before examining the subjects. The gel was then applied to one eye area according to the numbered list. After two minutes had elapsed, the first assistant was asked to go back and check the subject's eyes by comparing them to the first drawing. She then made a second drawing of the skin's appearance after the application of just the gel. When she had finished the second drawing, the second assistant applied a moisturizing lotion to the treated area and waited two more minutes. The first assistant then checked the area again a-ad drew the third and final diagram Seven different formulas were tested by this procedure. These were as follows:

1. 0.25 grams (0.7% w/v) polyacrylamide/polyacrylate copolymer, 0.1% Germaben II in 37 ml water
2. 0.50 grams (1% w/v) polyacrylamide/polyacrylate copolymer 0.1% Germaben II in 50 ml water
3. 0.45 grams polyacrylamide/polyacrylate copolymer, 0.05 grams sodium polyacrylate,0.10% Germaben II in 50 ml water (9:1)
4. 0.40 grams polyacrylamide/polyacrylate copolymer, 0.10 grams sodium polyacrylate, 0.1% Germaben II in 50 ml water (4:1)
5. 0.30 grams polyacrylamide/polyacrylate copolymer, 0.15 grams sodium polyacrylate 0.1% Germaben II in 50 ml water (2:1)
6. 0.15 grams polyacrylamide/polyacrylate copolymer, 0.30 grams sodium polyacrylate, 0.1% Germaben II in 50 ml water (1:2)
7. 0.45 grams polyacrylamide/,polyacrylate copolymer, 0.05 grams glycerin, 0.1% Germaben II in 50 ml water (1:2)

Except for formula No. 6, containing a high level of sodium polyacrylate, all samples produced visible reductions in wrinkles and fine lines. The most dramatic results came from formulas No. 1 and 2 and the next in performance was Formula No. 3. In the first part of each test the gel produced a noticeable change in the skin's appearance. However, a significant improvement was noted after the application of the lotion.

Irritation—Each subject was asked to leave the gel on his/her skin and after an hour was asked whether there was any irritation. The question was asked again after four hours. After testing, all seven formulas, formula No. 3 was found to be the most effective with no reports of any irritation. All of the polyacrylamide/polyacrylate copolymer formulas worked very well in the reduction or removal of wrinkles, but there was one report of irritation after one hour. One subject felt some burning and her eye was "weepy." After determining that formula No. 3 (with a 9:1 ratio of polyacrylamide/polyacrylate copolymer to sodium polyacrylate) was the formula of choice, each subject was asked to try it again on their other eye for additional testing for efficacy and irritation. It performed well on each person and there were no complaints of irritation.

EXAMPLE 4

A formulation consisting of polyacrylamide/polyacrylate copolymer and FD&C Blue No. 2 in water produced a gel which 21 participants applied to their nails. All participants noticed increased hardness within one day,. Uniform color was acquired within two days. Application was easy, and only small amounts were required. Drying time was about 20 seconds. The gel was applied twice daily, morning and night. The gel did not appear to wash out of the nails when the hands were placed in soapy water. There was a residual effect for about five days after applications ceased. Each of the subjects completed a detailed questionnaire before the test, at 7, 14 and 21 days. The results were as follows:

| Question/Number of Respondants | | Pretest Responses | After 7 Days | After 14 Days | After 21 Days |
|---|---|---|---|---|---|
| A. | How would you describe your nails? | | NA | NA | NA |
| 1. | Healthy & strong - seldom break or split | 2 | | | |
| 2 | Average strength - break when hit or snagged | 4 | | | |
| B. | What is the most serious problem with your nails? | | NA | NA | NA |
| 1. | Breaking/Chipping | 6 | | | |
| 2. | Splitting & peeling | 7 | | | |
| 3. | Curling | 2 | | | |
| 4. | All of the above | 7 | | | |
| C. | What is the condition of your cuticles? | | NA | NA | NA |
| 1. | Excellent | 0 | | | |
| 2. | Good | 3 | | | |
| 3. | Fair | 4 | | | |
| 4. | Dry/cracked | 15 | | | |
| D. | What is the color of your nails? | | NA | NA | NA |
| 1. | Opaque/white. Color is even and uniform | 8 | | | |
| 2. | Transparent | 14 | | | |
| E. | Do your nails have: | | NA | NA | NA |
| 1. | Natural polished appearance | 0 | | | |
| 2. | Dull surface appearance | 15 | | | |
| 3. | Average shine | 7 | | | |
| A. | Have you noticed a change in appearance of your nails: | NA | | | |
| 1. | Color has become more uniform | | 9 | 12 | 10 |
| 2. | Color has become less uniform | | 0 | 2 | 0 |
| 3. | No change | | 13 | 8 | 11 |
| B. | Do your nails have: | NA | | | |
| 1. | More polished appearance | | 7 | 16 | 11 |
| 2. | Less polished appearance | | 0 | 2 | 2 |
| 3. | No change | | 15 | 4 | 8 |
| C. | Do your nails appear to be: | NA | | | |
| 1. | Stronger/harder | | 16 | 19 | 19 |
| 2. | Weaker | | 0 | 0 | 0 |
| 3. | No change | | 6 | 2 | 2 |
| D. | Splitting and peeling has: | NA | | | |
| 1. | Increased | | 0 | 0 | 0 |
| 2. | Decreased | | 18 | 16 | 7 |
| 3. | Stopped completely | | 2 | 6 | 13 |
| 4. | No change | | 2 | 0 | 1 |
| E. | Breakage of the nails has: | NA | | | |
| 1. | Increased | | 0 | 0 | 0 |
| 2. | Decreased | | 15 | 15 | 11 |
| 3. | Stopped completely | | 3 | 7 | 8 |
| 4. | No change | | 4 | 0 | 2 |

-continued

| Question/Number of Respondants | | Pretest Responses | After 7 Days | After 14 Days | After 21 Days |
|---|---|---|---|---|---|
| F. | Is the condition of your cuticles: | NA | | | |
| 1. | Improved | | 16 | 17 | 14 |
| 2. | Worsened | | 2 | 0 | 0 |
| 3. | No change | | 4 | 5 | 7 |
| G. | Is there a visible difference on the tested hand? | NA | | | |
| 1. | Yes | | 15 | 18 | 20 |
| 2. | No | | 7 | 4 | 1 |
| H. | Would you purchase this product? | NA | NA | NA | |
| 1. | Yes | | | | 19 |
| 2. | No | | | | 2 |

CONCLUSIONS, RAMIFICATIONS, AND SCOPE

Thus, the inventive composition, when applied twice daily for one week, produced measurable improvements in uniformity of color, transparency, polished appearance, strength and hardness, decreased splitting, peeling, and breakage, condition of cuticles. It was a commercially' viable composition.

The embodiments illustrated and discussed in this specification are intended only to teach those skilled in the art the best way known to the inventors to make and use the invention. Nothing in this specification should be considered as limiting the scope of the present invention. Modification and variations of the above-described embodiments of the invention are possible without departing from the invention, as appreciated by those skilled in the art in light of the above teachings. It is therefore to be understood that, within the scope of the claims and their equivalents, the invention may be practiced other-wise than as specifically described.

What is claimed is:

1. A cosmetic composition comprising an effective amount of superabsorbent ionic polyacrylamide/polyacrylate copolymer alone or in admixture with sodium polyacrylate, said polymers being homogeneously distributed in a topically acceptable vehicle containing preservative, the composition having a cosmetically acceptable consistency, being free of components that would cause unacceptable irritation when applied to the skin, and being effective to immediately and temporarily reduce the appearance of wrinkles when applied to the skin and allowed to dry, wherein longer-term use of the product (from a few hours up to 9 weeks) reduces skin dryness, improves skin elasticity and skin pigmentation, the cosmetically acceptable consistency being obtained through pulverizing the polymer mixture, pouring same into carrier vehicle and subjecting the mixture of same in the carrier vehicle to sonication.

2. The composition of claim 1, wherein the composition is free of oily components.

3. The composition of claim 1, wherein the polymers are combined in powder form.

4. The composition of claim 1, wherein the polymers are water-soluble.

5. The composition of claim 1, wherein the preservative is selected from the group consisting of diazolidinyl urea, methylparaben, propylparaben, propylene glycol, and combinations thereof.

6. The composition of claim 1, wherein the superabsorbent polymer comprises a mixture of polyacrylamide/polyacrylate copolymer and sodium polyacrylate in a ratio ranging from about 10:1 to about 1:1.

7. The composition of claim 1, wherein the superabsorbent polymer comprises a mixture by weight from about 33% to about 100% polyacrylamide/polyacrylate copolymer and about 0% to about 67% sodium polyacrylate.

8. The composition of claim 1, wherein the vehicle is water and the superabsorbent polymer is in a concentration by weight between 0.1% and about 10%.

9. The composition of claim 1, wherein the vehicle is water and the superabsorbent polymer is in a concentration by weight between about 0.7% and 1%.

10. The composition of claim 1, wherein the superabsorbent polymer comprises a mixture of polyacrylamide/polyacrylate copolymer and sodium polyacrylate in a ratio of about 9:1, the vehicle is water, and the superabsorbent polymer is in a concentration by weight between about 0.7% and about 1%.

11. The composition of claim 1, labelled for use as a cosmetic, and capable of dispensing an effective per unit amount of the composition.

12. A cosmetic composition of claim 1, being effective to harden nails after repeated application for several days.

13. A method for making a cosmetic composition of claim 1 comprising:

preparing an aqueous base solution containing preservative, obtaining a finely ground superabsorbent polyacrylamide/polyacrylate copolymer alone or in admixture with sodium polyacrylate, combining the polymer with the aqueous base, and mixing the combination to produce a composition, the components of the composition being non-irritating when combined, being free of components that would cause unacceptable irritation when applied to the skin, and being effective to immediately and temporarily reduce the appearance of wrinkles when applied to the skin and allowed to dry, wherein longer-term use of the product (from a few hours up to 9 weeks) reduces skin dryness, improves skin elasticity and skin pigmentation, the cosmetically acceptable consistency being obtained through pulverizing the polymer mixture, pouring same into carrier vehicle and subjecting the mixture of same in the carrier vehicle to sonication.

* * * * *